(12) United States Patent
Smith

(10) Patent No.: US 12,714,633 B1
(45) Date of Patent: Aug. 25, 2026

(54) MASSAGE ROLLER WITH FLUID RESERVOIR

(71) Applicant: William Smith, Jamaica Queens, NY (US)

(72) Inventor: William Smith, Jamaica Queens, NY (US)

( * ) Notice: Subject to any disclaimer, the term of this patent is extended or adjusted under 35 U.S.C. 154(b) by 798 days.

(21) Appl. No.: 17/980,025

(22) Filed: Nov. 3, 2022

(51) Int. Cl.
*A61H 15/00* (2006.01)
*A61F 7/00* (2006.01)

(52) U.S. Cl.
CPC ....... *A61H 15/0092* (2013.01); *A61F 7/0085* (2013.01); *A61F 2007/0059* (2013.01); *A61F 2007/0063* (2013.01); *A61H 2015/0042* (2013.01); *A61H 2201/0207* (2013.01); *A61H 2201/0214* (2013.01); *A61H 2201/0242* (2013.01); *A61H 2201/1635* (2013.01)

(58) Field of Classification Search
CPC .... A61H 15/00; A61H 15/0092; A61H 15/02; A61H 2015/0007; A61H 2015/0042; A61H 2201/0207; A61H 2201/0214
See application file for complete search history.

(56) References Cited

U.S. PATENT DOCUMENTS 1,882,370 A * 10/1932 Schroeder .......... A61H 15/0092 601/19
2,546,095 A * 3/1951 Gustlin .................. A61H 15/02 601/19
2,787,261 A * 4/1957 Mcdonald .............. A45D 40/00 601/19
3,388,560 A 6/1968 Zhu et al.
4,884,560 A * 12/1989 Kuracina ........... A61H 15/0092 D24/207
5,251,620 A 10/1993 Boucher et al.
2002/0193714 A1* 12/2002 Pecora ................... A61H 15/00 601/121
2012/0265106 A1* 10/2012 Accardo ............ A61H 15/0092 601/123
2018/0078447 A1* 3/2018 Viner ...................... A61H 15/02
2021/0298988 A1* 9/2021 Watts-Russell .... A61H 15/0092

FOREIGN PATENT DOCUMENTS

DE 4447334 A1 * 7/1996 ......... A61H 15/0092

* cited by examiner

*Primary Examiner* — Douglas Y Sul
(74) *Attorney, Agent, or Firm* — Sanchelima & Associates, P.A.; Christian Sanchelima; Jesus Sanchelima

(57) ABSTRACT

A massage roller with fluid reservoir including a roller assembly with a first handle assembly and a second handle assembly attached to the sides thereof. The roller assembly includes a roller which has a pliable portion allowing it to conform with an area of a user's body when applying massage with said roller. The first handle assembly includes a first handle with a delivery fluid tube to insert hot/cold water by an aperture and store the hot/cold water in a reservoir located in the inner of the roller. The second handle includes a second handle which is configured in addition with the first handle to hold the roller through the lateral sides allowing it to deliver a massage to the area of the user's body.

6 Claims, 4 Drawing Sheets

MASSAGE ROLLER WITH FLUID RESERVOIR

BACKGROUND OF THE INVENTION

1. Field of the Invention

The present invention relates to a massage roller with fluid reservoir and, more particularly, to a massage roller with fluid reservoir that can store heated or cooled fluid to apply thermal massaged by a ball roller having a pair of handles attached to the lateral sides thereof.

2. Description of the Related Art

Several designs for massage rollers have been designed in the past. None of them, however, include a spherical massage roller which can be filled with hot/cold water through one of his handles.

Applicant believes that a related reference corresponds to U.S. Pat. No. 8,388,560 issued for a rolling massage device with a cylindrical body that can be filled with a thermal media such as water. Applicant believes that another related reference corresponds to U.S. Pat. No. 5,251,620 issued for a foot massaging device with massaging rollers that can be soaked in hot water. None of these references, however, teach of a thermal massage rolling device that is comprised of a spherical massage roller with a pair of handles and an internal reservoir that can be filled with a heated or cooled fluid to apply thermal therapy to a person's muscles.

Other documents describing the closest subject matter provide for a number of more or less complicated features that fail to solve the problem in an efficient and economical way. None of these patents suggest the novel features of the present invention.

SUMMARY OF THE INVENTION

It is one of the objects of the present invention to provide a heat/cold application massage on an area of a user's body.

It is another object of this invention to provide an easy roll and drag massage technique by a ball shaped roller.

It is another object of this invention to provide a help to cure the general chronic pain and the increase and decrease of the blood flow.

It is still another object of the present invention to provide a pliable portion with bubbles on the exterior of the roller configured to provide deep muscle penetration and pockets of energy.

It is yet another object of this invention to provide such a device that is inexpensive to implement and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

Figure 1:
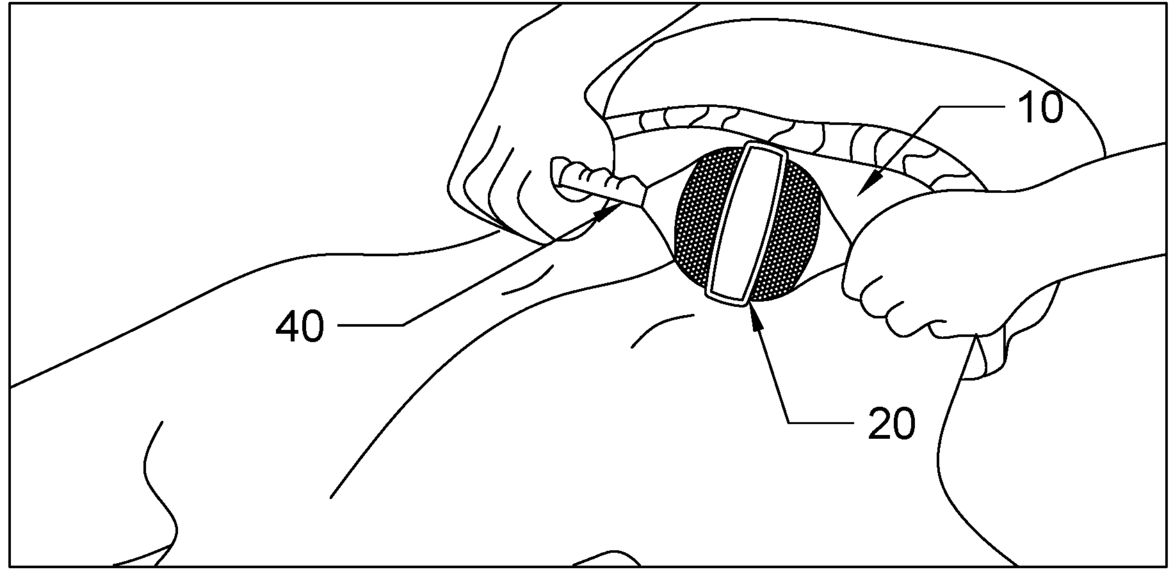
FIG. 1 represents an operational view of the present invention. 10.

Referring now to the drawings, where the present invention is generally referred to with numeral 10, it can be observed that it basically includes a roller assembly 20, a first handle assembly 40 and a second handle assembly 60. It should be understood there are modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

The roller assembly 20 includes a roller 22, a reservoir 24, a pressure portion 24, a central portion 25, a pliable portion 26 and frame portions 28. The roller 22 in a suitable embodiment, may have a ball shape as best observed in FIG. 1. Nevertheless, in another embodiment, the roller 22 may have a hollow oval body. In a preferred embodiment, the roller 22 may have a hollow body to allow storing the reservoir 24. The roller 24 may be suitable to be made of a plastic material. Nevertheless, other materials like, polyethylene foam, rubber, expanded polypropylene or any other variation thereof. The roller 22 may have attached the first handle assembly 40 and the second handle assembly 60 on the sides. It may be considered that the roller 22 includes the reservoir 24 which may be suitable to have a body that conforms with the inner shape of the roller 22, the roller 22 may cover the entire reservoir 24. It is to be considered that the roller 22 may be configured to provide a deep massage to an area of the part of a user's body allowing it to help with general chronic pain and the blood flow. In another embodiment, the roller 22 may also be configured to roll over the user's body applying the hot/cold water thereof in cooperation with the central portion 25 and the pressure portion **24*a* which may permit the hot/cold water be deeply applied to the user's skin. In a suitable embodiment, the reservoir 24 may be made of a plastic material. In another embodiment the reservoir 24 may be made of a rubber material, expanded polypropylene or the like. It may be considered that the inner contour of the reservoir 24 may be wrapped with a silicone material to provide comfort to the user while in use. The reservoir 24 may be configured as a delivering reservoir which allows storing cold/hot water. In a preferred embodiment, the pressure portion 24*a* may be suitable to be placed along a perimeter of the central portion 25. The pressure portion 24*a* may be suitable to be made of a silicone material which is wrapped along an exterior portion of the roller 24 surrounding the perimeter of the central portion 25 wherein the reservoir 24 can be shown. In a suitable embodiment, the pressure portion 24 may be configured to be applied to the user's body in cooperation with the central portion 25. In a preferred embodiment the central portion 25** may be configured to be applied to the user's skin in a direct contact.

Figure 2:
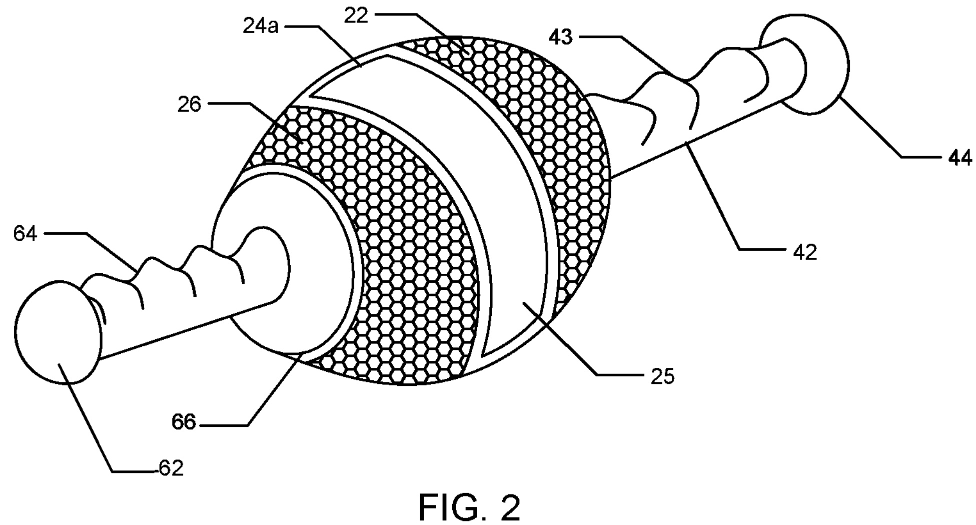
FIG. 2 shows a perspective view of a roller 22 with a first handle 42 and a second handle 62 attached to the sides thereof.
Figure 4:
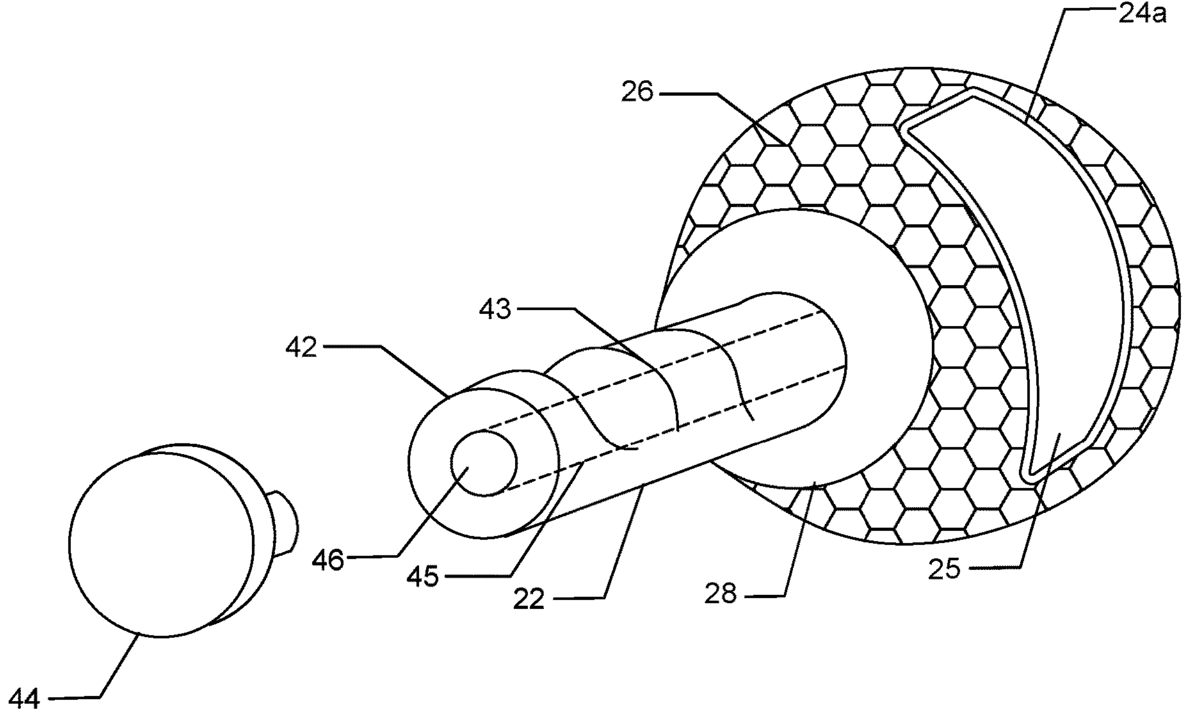
FIG. 4 is a representation of an enlarged view of the first handle 42 and the roller 22.

In a preferred embodiment, the pliable portion 26 may partially cover the exterior of the roller 22. Nevertheless, in another embodiment, the pliable portion 26 may entirely cover the exterior of the roller 22. As best observed in FIG. 4 the pliable portion 26 may be covered by bubbles configured to provide a deep muscle penetration when making a massage in cooperation with the central portion 25 and the pressure portion 24*a*. As best observed in FIG. 2 the pliable portion 26 may have a curved body which covers the curved shape of the roller 22. In a suitable embodiment, the pliable portion 26 may be configured to deliver a comfortable massage to the user when rolling the roller 22 along the part of the user's body allowing the pliable portion 26 to conform with the shape of the user's body when applying force thereof. The pliable portion 26 may be made of a pliable plastic material or any variation of soft plastic.

Figure 3:
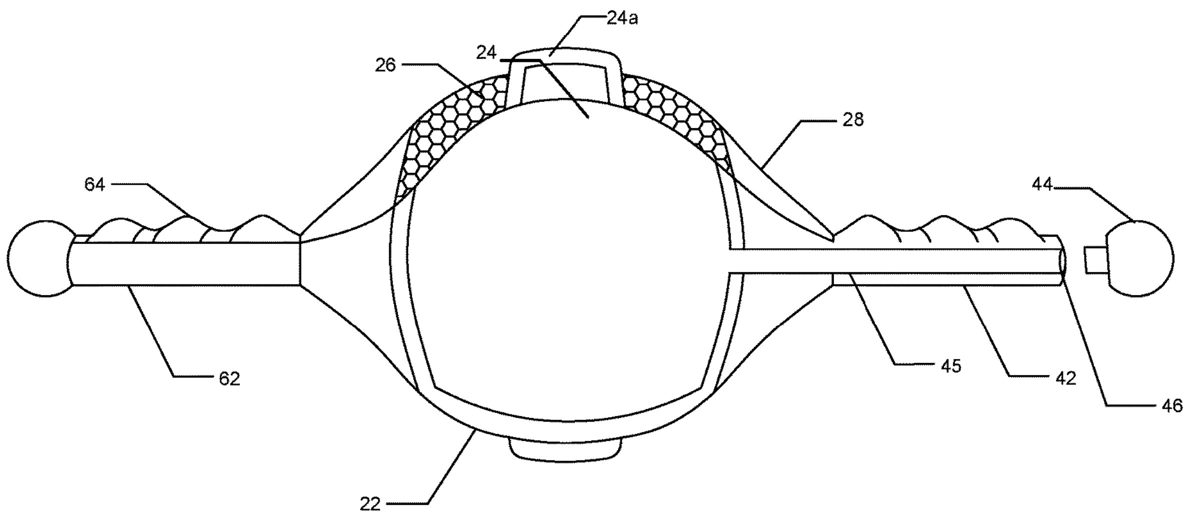
FIG. 3 illustrates a front sectional view of the roller 22 with the first handle 42 and second handle 62 attached thereof. A reservoir 24 is placed within the roller 22.

As best observed in FIG. 3 the frame portions 28 may be attached to the roller 22 wherein each of the frame portions 28 may be attached to a side of the roller 22. The frame portions 28 may be suitable to have a shape that conforms with the lateral sides of the roller 22. In a suitable embodiment, the frame portions 28 may allow the first handle assembly 40 and the second handle assembly 60 to attach to the roller 22 considering that the lateral side of the frame portions 28 may have a shape that conforms with the lateral side of the first handle assembly 40 and the second handle assembly 60. In a suitable embodiment, the frame portions 28 may be configured to stabilize the roller 22 when massaging the area of a user's body.

The first handle assembly 40 includes a first handle 42, a first gripping portion 43, a screw cap 44, a fluid tube 45 and an aperture 46. The first handle 42 may have a hollow cylindrical body that conforms with at least one of the frame portions 28. The first handle 42 may be made of a soft rubber material. Nevertheless, in other embodiments, materials like plastic, wood, steel, metal, aluminum, polymers or any other variation thereof, may be suitable for the first handle 42. It is to be considered that the first portion 42 may have the first gripping portion 43 attached on a top surface thereof. The first gripping portion 43 may be made of a material that the first handle 42 may be made of. The first handle 42 may include a fluid tube 45 placed therein and an aperture 46. The aperture 46 may be configured as a liquid delivery to dump the hot/cold water passing through the fluid tube 45 which may be configured to deliver the hot/cold water to the reservoir 24. It is to be considered that fluid tube 45 may be interconnected with the reservoir 24. In a preferred embodiment, the first handle 42 may be configured to grab the roller 22 which is attached to the side by at least one of the frame portions 28.

As observed in FIG. 3 the frame portions 28 may be suitable to be configured as the distal ends of the roller 22. In a suitable embodiment the fluid tube 45 may be made of a pliable plastic material considering that the aperture 46 may be a side entrance of the fluid tube 45 the aperture 46 may also be made of a pliable plastic material. The first handle 42 may be sealed by the screw cap 44 by a distal end as best observed in FIG. 2. In a suitable embodiment, the screw cap 44 may have a cylindrical body that conforms with the shape of the aperture 46. The screw cap 44 may be configured to seal the aperture 46 when liquid of hot/cold water is stored in the reservoir 24. It is to be understood that the aperture 46 may have a circular shape that conforms with the shape of the fluid tube 45. The screw cap 44 in one embodiment may be a screw cap. Nevertheless, in another embodiment, the screw cap 44 may be a plastic cork which may seal the aperture 46. It is to be considered that the first handle 42 may be configured as a gripping portion and also to insert liquid into the reservoir 24 through the fluid tube 45.

The second handle assembly 60 includes a second handle 62 and a gripping portion 64. In a suitable embodiment, the second handle 62 may be configured to grab the roller 22 in addition with the first handle 42. It is to be considered that the second handle 62 may have a cylindrical body wherein the lateral side thereof may conform with the shape of at least one of the frame portions 28. The second handle 62 may be made of a soft rubber material. Nevertheless, in other embodiments, materials like plastic, wood, steel, metal, aluminum, polymers or any other variation thereof, may be suitable for the second handle 62. The second handle 62 may be attached on the opposite side of the first handle 42. In a suitable embodiment, the second handle 62 may have the gripping portion 64 that entirely covers the top surface of the second handle 62. It is to be considered that the gripping portion 64 may be made of a material that second handle 62 may be made of. The gripping portion 64 may be suitable to allow the user to grab the roller 22 in practical configuration.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A massage roller with fluid reservoir, comprising:

a roller assembly including a roller having a spherical ball-shaped hollow body with a curved exterior surface, said roller including a reservoir configured to store hot or cold water within an inner hollow portion of said roller, said roller including a pliable portion having a curved body conforming to said curved exterior surface of said roller and partially covering a portion of said curved exterior surface, said pliable portion including bubbles on an exterior surface thereof configured to provide deep muscle penetration, wherein a central portion of the roller is not covered by the pliable portion and configured to be applied to a user's skin in direct contact said roller including a pair of frame portions wherein each frame portion is attached to opposite lateral sides of said roller, said frame portions having a shape conforming to said lateral sides of said roller;

a first handle assembly including a first handle having a hollow cylindrical body attached to one of said frame portions at one lateral side of said roller, said first handle including a first gripping portion on a top surface thereof, said first handle including a fluid tube extending concentrically along said first handle and interconnected with said reservoir, said fluid tube including an aperture positioned as a side entrance to said fluid tube, and a screw cap configured to seal said aperture; and a second handle assembly including a second handle having a cylindrical body attached to another one of said frame portions at an opposite lateral side of said roller, said second handle including a second gripping portion entirely covering a top surface of said second handle, wherein said first handle and said second handle are positioned opposite to each other on said lateral sides of said roller.

2. The massage roller with fluid reservoir of claim 1, wherein said pliable portion is made of a pliable plastic material and partially covers said curved exterior surface of said roller.

3. The massage roller with fluid reservoir of claim 1, wherein said frame portions are made of a hard impact plastic material and are configured to stabilize said roller when massaging an area of a user's body.

4. The massage roller with fluid reservoir of claim 1, wherein said first handle and said second handle are made of a soft rubber material.

5. The massage roller with fluid reservoir of claim 1, wherein said reservoir is wrapped with a silicone material on an inner contour thereof to provide comfort to a user while in use.

6. A massage roller with fluid reservoir, consisting of:

a roller assembly including a roller having a spherical ball-shaped hollow body with a curved exterior surface, said roller including a reservoir having a body conforming to an inner shape of said roller and configured to store hot or cold water, said roller including a pliable portion having a curved body conforming to said curved exterior surface and partially covering said curved exterior surface of said roller, said pliable portion including bubbles on an exterior surface thereof configured to provide deep muscle penetration, wherein a central portion of the roller is not covered by the pliable portion and configured to be applied to a user's skin in direct contact said roller including a pair of frame portions wherein each frame portion is attached to opposite lateral sides of said roller and has a shape conforming to said lateral sides of said roller, said frame portions made of a hard impact plastic material;

a first handle assembly including a first handle having a hollow cylindrical body with a lateral side conforming to a shape of one of said frame portions and attached to said one frame portion at one lateral side of said roller, said first handle including a first gripping portion on a top surface thereof, said first handle including a fluid tube extending concentrically entirely along said first handle and interconnected with said reservoir, said fluid tube including an aperture positioned as a side entrance to said fluid tube configured to insert liquid therethrough to said reservoir, and a screw cap having a cylindrical body conforming to a shape of said aperture and configured to seal said aperture; and a second handle assembly including a second handle having a cylindrical body with a lateral side conforming to a shape of another one of said frame portions and attached to said another frame portion at an opposite lateral side of said roller, said second handle including a second gripping portion entirely covering a top surface of said second handle, wherein said first handle and said second handle are positioned opposite to each other on said lateral sides of said roller and are configured to allow a user to grab said roller by said frame portions.

* * * * *